United States Patent [19]

Schmidt et al.

[11] 4,351,908

[45] Sep. 28, 1982

[54] PROCESS FOR THE MANUFACTURE OF ACETIC ACID, ACETIC ALDEHYDE AND ETHANOL FROM SYNTHESIS GAS

[75] Inventors: Hans-Joachim Schmidt, Königstein; Ernst I. Leupold, Neu-Anspach, both of Fed. Rep. of Germany

[73] Assignee: Hoechst Aktiengesellschaft, Frankfurt am Main, Fed. Rep. of Germany

[21] Appl. No.: 310,073

[22] Filed: Oct. 9, 1981

[30] Foreign Application Priority Data

Oct. 11, 1980 [DE] Fed. Rep. of Germany ....... 3038448

[51] Int. Cl.$^3$ ............................................... C07C 27/06
[52] U.S. Cl. ...................................... 518/716; 518/714
[58] Field of Search ................................. 518/716, 714

[56] References Cited

U.S. PATENT DOCUMENTS

| | | | |
|---|---|---|---|
| 4,224,236 | 9/1980 | Wunder et al. | 518/716 |
| 4,288,558 | 9/1981 | Schmidt et al. | 518/716 |

*Primary Examiner*—Howard T. Mars
*Attorney, Agent, or Firm*—Curtis, Morris & Safford

[57] ABSTRACT

The invention provides a process for the manufacture of acetic acid, acetic aldehyde and ethanol by reaction in the gaseous phase of carbon monoxide and hydrogen in the presence of catalysts containing rhodium and optionally promoters, at elevated temperature and pressure. In this process, the temperature is raised in the starting phase, where the catalyst is heated to the working temperature $T_R$ intended for continuous operation, in a range of from $T_O$ to $T_R$, $T_O$ being 75° to 125° C. below $T_R$, continuously or in steps of 10° C. at most, in a period of time of from 100 to 1,000 hours; the temperature being raised by 10° C. at most within any 10 hour interval.

2 Claims, No Drawings

PROCESS FOR THE MANUFACTURE OF ACETIC ACID, ACETIC ALDEHYDE AND ETHANOL FROM SYNTHESIS GAS

The invention provides a process for the manufacture of acetic acid, acetic aldehyde and ethanol by reaction in the gaseous phase of carbon monoxide and hydrogen in the presence of catalysts containing rhodium and optionally promoters, at elevated temperature and pressure.

Such processes are state of the art. It is furthermore known that addition of promoters increases the activity and/or the selectivity towards the individual compound. Processes of such kind are described in German Auslegeschriften Nos. 2,503,204, 2,503,233, 2,628,463, German Offenlegungsschriften Nos. 2,628,576, 2,712,732, 2,814,365, 2,846,148, and U.S. Pat. Nos. 4,096,164, 4,101,450, 4,136,104 and 4,162,262.

However, the catalyst life is often still insufficient in these processes.

In German Offenlegungsschriften Nos. 2,825,495, 2,825,598, 2,850,110 and 2,850,201, measures have therefore been described which are taken in order to bring about an improved catalyst life, and which consist in feeding magnesium salts or compounds or hydrogen halides or compounds thereof continuously or discontinuously to the reaction zone. The result is an essential improvement of stability. However, this result is attained by means of these cited promoters only, and they require in general additional apparatus for dosage and evaporation of the additives.

It has now been found that the life of the rhodium catalysts can be prolonged in simple manner by raising the temperature in the starting phase of the process, where the catalyst is heated, within the range of the last 75 to 125° C. before attaining the working temperature continuously or in little steps, and within a period of time of from 100 to 1,000 hours. Thus, not only the life of the catalyst is considerably prolonged, but also an increased selectivity towards the intended oxygen-containing $C_2$ compounds is the result. In particular, the selectivity to acetic acid increases first and remains constant after the reaction temperature is attained, while the selectivity towards methane decreases somewhat at the start.

Subject of the invention is therefore a process for the manufacture of acetic acid, acetic aldehyde and ethanol by reaction in the gaseous phase of carbon monoxide and hydrogen in the presence of catalysts containing rhodium and optionally promoters, at elevated temperature and pressure, which comprises raising the temperature in the starting phase of the process, where the catalyst is heated to the working temperature $T_R$ intended for continuous operation, in a range of from $T_O$ to $T_R$, $T_O$ being 75° to 125° C. below $T_R$, continuously or in steps of 10° C. at most, in a period of time of from 100 to 1,000 hours; the temperature being raised by 10° C. at most within any 10 hour interval. Preferably, the temperature is raised within a period of time of from 120 to 800 hours.

Thus, it has become evident that in the starting phase of the synthesis gas reaction the speed of heating is of decisive importance for the life of the catalyst and the selectivity towards the oxygen-containing $C_2$ compounds. It is essential that the temperature is raised within the range of 75° to 125° C. below the working temperature $T_R$ in little steps of 10° C. at most and in a period of time of from 100 to 1000 hours. Furthermore, within any 10 hours interval during this period the temperature must not be raised by more than 10° C.

It was not to be expected that the delayed heating speed in the temperature range of from $T_O$ to $T_R$ according to the invention would result in increase of life and selectivity of the catalyst. For, although during the prolonged heating phase alterations of the catalyst structure are expected to occur in a kinetically controlled reaction at the low temperature, the subsequent longlasting influence of the higher working temperature was supposed to result in the same thermodynamically favorable structure which the catalyst adopts without the pretreatment according to the invention.

By working temperature $T_R$, there is to be understood that temperature at which an advantageous and economic conversion of the synthesis gas to the oxygen-containing compounds, that is, acetic acid, acetic aldehyde and ethanol, occurs in continuous operation. Depending on the catalyst composition, the catalyst preparation, the kind and amount of promoters, and depending on the other reaction conditions such as pressure, volume/space velocity and composition of the gases fed in, this temperature may vary within wide limits. Generally, $T_R$ is in the range of from 200° to 450° C., preferably 250° to 375° C. The operational pressure is generally from 1 to 300, preferably 20 to 200, bar.

For the reaction of synthesis gas according to the invention, catalysts are used which contain on a carrier from 0.1 to 15 weight %, preferably 0.5 to 10 weight %, of rhodium in the form of metal or in a valence stage of below 3, that is, as complex compound of zerovalent rhodium or as salt or complex compound of mono- or bivalent rhodium. Optionally, the catalysts may contain furthermore promoters or activators, especially magnesium in combination with halide ions, and manganese. Moreover, substances may be present which influence the selectivity towards the individual oxygen-containing products, such as iron, zirconium, hafnium, lanthanum, platinum, mercury, molybdenum, tungsten, uranium or thorium.

As carriers, commercial carrier materials having different specific surface may be used, preferably those having a specific surface of from 50 to 1,000 m$^2$/g. Suitable are for example silicic acid, silicates, aluminum oxide, titanium oxide, zirconium oxide, zeolites, thorium oxide or spinels.

For carrying out the process of the invention, the catalyst is introduced into the reaction zone and first heated at any desired speed to a temperature $T_O$ which is 75° to 125° C. below the intended working temperature $T_R$. The temperature raise from $T_O$ to $T_R$ is then carried out by heating continuously or in temperature intervals of 10° C. at most; the time of this temperature raise from $T_O$ to $T_R$ being in a range of from 100 to 1,000, preferably 120 to 800, hours. For example, in the case where the working temperature is 300° C., the catalyst is heated to a temperature between 175° and 225° C., and the further heating is then slowed down in such a manner that the working temperature of 300° C. is attained after a time in the range of from 100 to 1,000 hours.

While heating under normal or elevated pressure, synthesis gas or an inert gas such as nitrogen, or a mixture of these gases is passed over the catalyst under the intended operational pressure before reaching the low temperature $T_O$, in order to prevent a too rapid temperature rise at the start of the reaction in the temperature range of $T_O$ to $T_R$ important for the process of the invention.

For carrying out the process, usual solid bed reactors may be used.

It is advantageous in this case to keep the thickness of the catalyst layer low in order to ensure a good heat dissipation. Suitable are furthermore reactors with moving catalyst bed or fluidized bed reactors. A preferred embodiment of the invention provides carrying out the reaction in a circulating gas apparatus, where after separation of the condensable reaction products the unreacted gas mixture is recycled to the reactor after addition of fresh synthesis gas.

Suitable circulating gas apparatus are those provided with interior or external gas circulation.

The following examples illustrate the invention without limiting its scope in any way. The indicated gas amounts are relative to normal conditions. The indicated space time yields (STY) in grams per liter of catalyst and hour are relative to the sum of acetic acid AcOH, acetic aldehyde AcH and ethanol EtOH.

COMPARATIVE EXAMPLE 1

First, a catalyst is prepared as follows: 100 g of silic acid (grain size 1-3 mm) having a bulk density of 0.42 kg/l and a BET surface of 270 m²/g are impregnated with a solution of 2.5 g $MgCl_2 \cdot 6 H_2O$ in 110 ml of water, dried for 2 hours at 80° C. and for 2 hours at 150° C., and subsequently sintered for 30 minutes at 800° C. After cooling, the catalyst is impregnated with a solution of 8 g of $RhCl_3 \times H_2O$ (37.8 weight % of Rh) in 100 ml of water, and dried as indicated above. The catalyst is then reduced by passing 50 l/h of hydrogen over it at 250° C. under normal pressure. It contains 2.8 weight % of Rh, 0.25 weight % of Mg and 1.4 weight % of Cl.

100 ml (45 g) of this catalyst are introduced into a reaction tube having a length of 1 m and an inner diameter of 16 mm, and provided with a coaxially arranged thermometer tube having an outer diameter of 6 mm. After flushing of the apparatus with nitrogen, a pressure of 80 bar is adjusted by means of a carbon monoxide/hydrogen mixture (volume ratio 1:1), and the catalyst is heated by passing over it 200 l/h of the above synthesis gas. After 2.5 hours, a catalyst temperature of 200° C. is attained, after a total of 4 hours the temperature is 250° C., and after a total of 7.5 hours, the working temperature of 300° C. is reached.

Further 200 l/h of synthesis gas (carbon monoxide and hydrogen in a volume ratio of 1:1) are passed over the catalyst at 80 bar and 300° C. The reaction mixture is cooled to 5° C. in a brine-cooled condenser, and the uncondensed residual gas is depressurized via a valve. Condensate and off-gas are analyzed by gas chromatography. The following space/time yields and selectivities, relative to converted CO, are the result:

| Operating Time h | Temp. °C. | STY g/l.h | Selectivities (mol %) | | | |
|---|---|---|---|---|---|---|
| | | | AcOH | AcH | EtOH | CH₄ |
| 4 | 250 | 170 | 76 | 5 | 1.5 | 9 |
| 7.5 | 300 | 380 | 70 | 7 | 2.3 | 13 |
| 100 | 300 | 375 | 68 | 7 | 3.5 | 16 |
| 1280 | 300 | 290 | 61 | 9 | 6.0 | 18 |

Remaining CO is converted to carbon dioxide and high molecular weight oxygen-containing compounds.

EXAMPLE 1

100 ml of fresh catalyst composed as described in Comparative Example 1 are heated within 2.5 hours to 200° C., and then within 200 hours at a rate of temperature raise of 5° C. in 10 hours each to 300° C. The other conditions being maintained as described for Comparative Example 1, the following space/time yields and selectivities are the result:

| Operating Time h | Temp. °C. | STY g/l.h | Selectivities (mol %) | | | |
|---|---|---|---|---|---|---|
| | | | AcOH | AcH | EtOH | CH₄ |
| 102.5 | 250 | 180 | 64 | 10 | 5 | 12 |
| 200 | 300 | 385 | 75 | 6 | 3 | 9 |
| 1280 | 300 | 375 | 76 | 5 | 3 | 10 |

EXAMPLE 2

Operations are as in Example 1, but the catalyst temperature is raised from 200° C. on at a rate of temperature raise of 2° C. in 10 hours each to 300° C. within 500 hours. At this latter moment the space/time yield is 370 g/l.h and after a total of 1280 hours it is still 355 g/l.h at unchanged selectivity towards acetic acid.

COMPARATIVE EXAMPLE 2

The catalyst is prepared as follows: 100 g of silicic acid having a BET surface of 270 m²/g and a pore volume of 1.22 ml/g are impregnated with a solution of 11.1 g of $RhCl_3 \times H_2O$ (37.8 weight % of Rh) in 115 ml of water, dried for 4 hours at 120° C. and reduced subsequently by passing over it 30 l/h of hydrogen for 3 hours at 450° C. under normal pressure. The catalyst contains 4.0 weight % of rhodium and 0.6 weight % of chlorine.

The apparatus is the same as in Comparative Example 1. 100 ml of the above catalyst are introduced into the reaction tube. After flushing of the apparatus with nitrogen, 200 l/h of a carbon monoxide/hydrogen mixture (volume ratio 1:1) are passed over the catalyst at 100 bar, and it is heated within 24 hours to 340° C. Then further 200 l/h of the gas mixture are passed over the catalyst at 100 bar and 340° C. The following space/time yields and selectivities are the result:

| Operating Time h | Temp. °C. | STY g/l.h | Selectivities (mol %) | | | |
|---|---|---|---|---|---|---|
| | | | AcOH | AcH | EtOH | CH₄ |
| 10 | 250 | 41 | 35 | 12 | 24 | 23 |
| 24 | 340 | 156 | 31 | 8 | 21 | 33 |
| 100 | 240 | 122 | 27 | 8 | 17 | 38 |
| 570 | 340 | 72 | 23 | 6 | 10 | 46 |

EXAMPLE 3

Operations are as in Comparative Example 2. After 10 hours (counted from the start of heating), a catalyst temperature of 250° C. is attained. Then the temperature is raised by 6° C. within 10 hours each only, so that after a total of 160 hours the working temperature of 340° C. as in comparative Example 2 is reached. The following space/time yields and selectivities are the result:

| Operating Time h | Temp. °C. | STY g/l.h | Selectivities (mol %) | | | |
|---|---|---|---|---|---|---|
| | | | AcOH | AcH | EtOH | $CH_4$ |
| 10 | 250 | 39 | 33 | 14 | 22 | 22 |
| 100 | 340 | 168 | 39 | 11 | 21 | 19 |
| 960 | 340 | 152 | 42 | 10 | 23 | 18 |

What is claimed is:

1. A process for the manufacture of acetic acid, acetic aldehyde and ethanol by reaction in the gaseous phase of carbon monoxide and hydrogen in the presence of catalysts containing rhodium and optionally promoters, at elevated temperature and pressure, which comprises raising the temperature in the starting phase of the process, where the catalyst is heated to the working temperature $T_R$ intended for continuous operation, in a range of from $T_O$ to $T_R$, $T_O$ being 75° to 125° C. below $T_R$, continuously or in steps of 10° C. at most, in a period of time of from 100 to 1,000 hours; the temperature being raised by 10° C. at most within any 10 hour interval.

2. The process as claimed in claim 1, which comprises raising the temperature in a period of time of 120 to 800 hours.

* * * * *